(12) United States Patent
Schneider et al.

(10) Patent No.: US 7,558,410 B2
(45) Date of Patent: Jul. 7, 2009

(54) FINGERPRINT SCANNING STATION

(75) Inventors: John K. Schneider, Snyder, NY (US); Jack C. Kitchens, Tonawanda, NY (US); Stephen M. Gojevic, Buffalo, NY (US)

(73) Assignee: Ultra-Scan Corporation, Amherst, NY (US)

( * ) Notice: Subject to any disclaimer, the term of this patent is extended or adjusted under 35 U.S.C. 154(b) by 0 days.

(21) Appl. No.: 11/242,194

(22) Filed: Oct. 1, 2005

(65) Prior Publication Data

US 2006/0115132 A1   Jun. 1, 2006

Related U.S. Application Data

(60) Provisional application No. 60/632,152, filed on Dec. 1, 2004.

(51) Int. Cl.
*G06K 9/00* (2006.01)
(52) U.S. Cl. .................. 382/126; 382/127; 600/459
(58) Field of Classification Search ............... 340/5.82, 340/5.83; 382/124, 125, 115, 126, 127; 356/71; 600/437, 459
See application file for complete search history.

(56) References Cited

U.S. PATENT DOCUMENTS

| | | | | |
|---|---|---|---|---|
| 4,537,484 A | * | 8/1985 | Fowler et al. | 396/15 |
| 4,545,386 A | * | 10/1985 | Hetz et al. | 600/462 |
| 4,783,167 A | * | 11/1988 | Schiller et al. | 356/71 |
| 4,811,414 A | * | 3/1989 | Fishbine et al. | 382/272 |
| 5,456,256 A | * | 10/1995 | Schneider et al. | 600/445 |
| 5,587,533 A | * | 12/1996 | Schneider et al. | 73/614 |
| 5,598,846 A | * | 2/1997 | Peszynski | 600/462 |
| 5,647,364 A | * | 7/1997 | Schneider et al. | 600/445 |
| 5,737,439 A | * | 4/1998 | Lapsley et al. | 382/115 |
| 5,818,956 A | * | 10/1998 | Tuli | 382/126 |
| 5,828,355 A | * | 10/1998 | Comeau et al. | 345/59 |
| 5,926,261 A | * | 7/1999 | Hoshino | 356/71 |
| 5,935,071 A | * | 8/1999 | Schneider et al. | 600/445 |
| 6,280,387 B1 | * | 8/2001 | Deforge et al. | 600/454 |
| 6,289,112 B1 | * | 9/2001 | Jain et al. | 382/116 |
| 6,296,610 B1 | * | 10/2001 | Schneider et al. | 600/445 |
| 6,355,937 B2 | * | 3/2002 | Antonelli et al. | 250/556 |
| 6,400,836 B2 | * | 6/2002 | Senior | 382/124 |
| 6,597,802 B1 | * | 7/2003 | Bolle et al. | 382/124 |
| 6,794,988 B1 | | 9/2004 | Weiss et al. | |
| 6,937,748 B1 | * | 8/2005 | Schneider et al. | 382/126 |
| 6,993,165 B2 | * | 1/2006 | McClurg et al. | 382/124 |
| 7,077,015 B2 | * | 7/2006 | Hayward et al. | 73/862.041 |
| 7,218,761 B2 | * | 5/2007 | McClurg et al. | 382/127 |
| 7,400,750 B2 | * | 7/2008 | Nam | 382/124 |

(Continued)

OTHER PUBLICATIONS

International Search Report and Written Opinion for PCT/2005/035554, filed Sep. 27, 2006, Ultra-Scan Corporation.

*Primary Examiner*—Gregory M Desire
(74) *Attorney, Agent, or Firm*—Hodgson Russ LLP

(57) ABSTRACT

The invention may be embodied as a fingerprint scanner having a housing, a curved-surface imaging system and a planar imaging system. The curved-surface imaging system may be capable of collecting information that may be used to produce a curved-surface image of a finger. The planar imaging system may be capable of collecting information that may be used to produce a planar image of one or more fingers at a time.

8 Claims, 6 Drawing Sheets

U.S. PATENT DOCUMENTS

| | | |
|---|---|---|
| 7,400,751 B2 * | 7/2008 | Schneider et al. ........... 382/124 |
| 2003/0125629 A1 * | 7/2003 | Ustuner ...................... 600/459 |
| 2003/0197853 A1 * | 10/2003 | Fenrich ...................... 356/71 |
| 2004/0034306 A1 * | 2/2004 | Seward ...................... 600/459 |
| 2005/0089204 A1 * | 4/2005 | Carver et al. ................ 382/127 |
| 2005/0105784 A1 * | 5/2005 | Nam .......................... 382/124 |
| 2006/0115132 A1 * | 6/2006 | Schneider et al. ........... 382/126 |
| 2006/0133651 A1 * | 6/2006 | Polcha et al. ............... 382/115 |

* cited by examiner

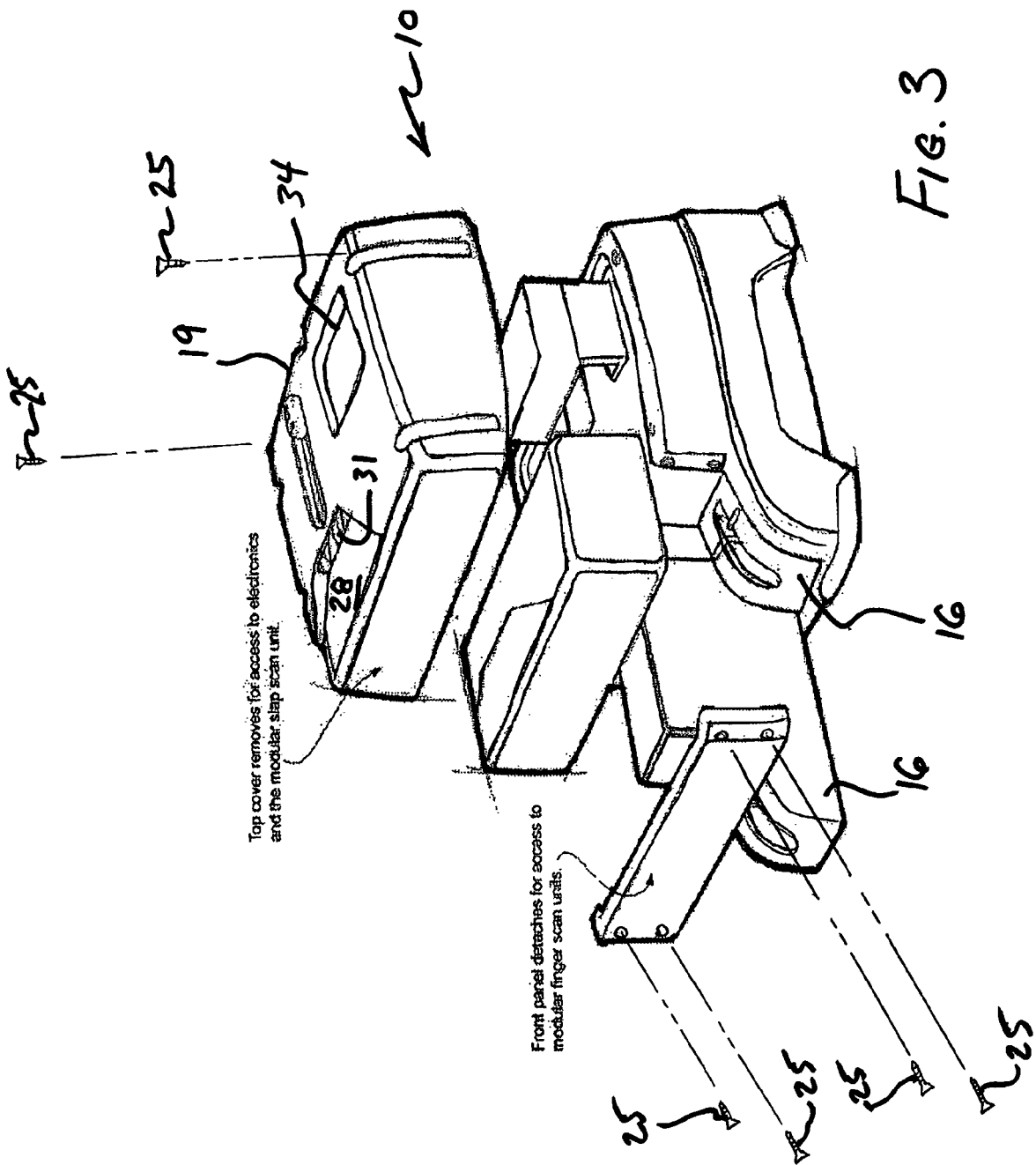

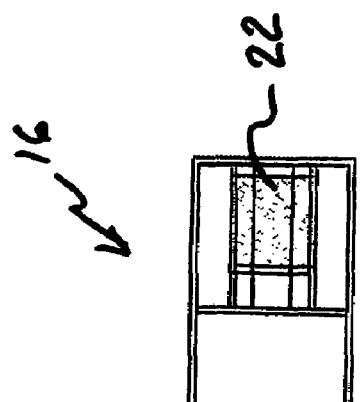
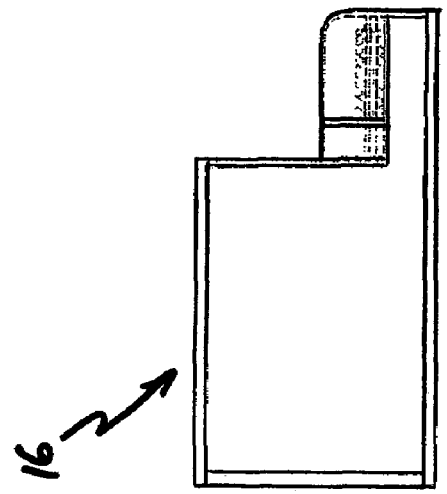
Fig. 4A
Fig. 4B
Fig. 4C

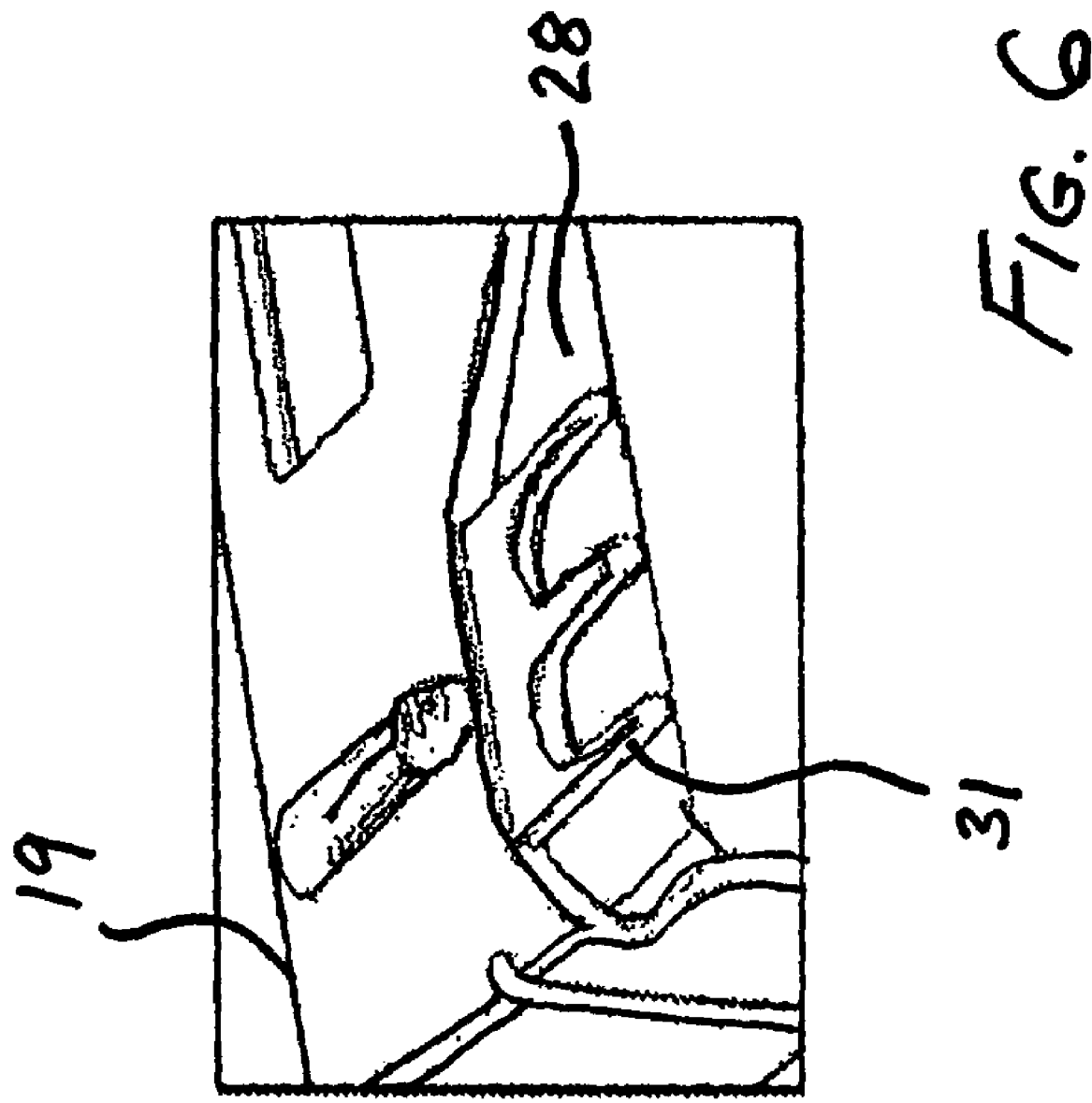

FINGERPRINT SCANNING STATION

CROSS-REFERENCE TO RELATED APPLICATION

This application claims the benefit of priority to U.S. provisional patent application Ser. No. 60/632,152, filed on Dec. 1, 2004.

FIELD OF THE INVENTION

The present invention relates to fingerprint scanners.

BACKGROUND OF THE INVENTION

Since the 1800's fingerprint information has been collected from human fingers and hands by means of ink and paper. For the purposes of this document, the term "fingerprint" is used to mean the skin surface friction ridge detail of a portion of a hand, such as a single fingerprint, or the entire hand. In recent years various electronic fingerprint scanning systems have been developed utilizing optical, capacitance, direct pressure, thermal and ultrasonic methods. Methods based on ultrasound have proven to be highly accurate, since they are insulated from the effects of grease, dirt, paint, ink and other image contaminants.

In ultrasonic fingerprint scanners, the ultrasound wave is started and stopped to produce a pulse. At each material interface encountered by the pulse, a portion of the pulse reflects. For example, the interface between a platen and skin or the interface between air and skin may each reflect a portion of the pulse. The reflected wave pulses may be detected by a detector. The elapsed time during which the pulse traveled from the ultrasound pulse emitter to the interface and back may be determined. The elapsed time may be used to determine the distance traveled by the pulse and its reflected wave pulses. By knowing the distance traveled by the pulse, the position of an interface may be determined.

There may be many interfaces encountered by the emitted pulse, and so there may be many reflected wave pulses. The approximate position of a finger being scanned may be known, and therefore the pulse reflected from the finger may be expected during a particular time interval. In a technique commonly referred to as "range gating", a detector may be configured to ignore reflected pulses that are not received during that time interval. The reflected signal may be processed and converted to a digital value representing the signal strength. The digital value may be used to produce a graphical display of the signal strength, for example by converting the digital values to a gray-scale bitmap image, thereby producing a contour map of the finger surface which is representative of the depth of the ridge structure detail.

SUMMARY OF THE INVENTION

The present invention may be embodied as a device capable of scanning fingerprints. Ultrasound may be used as the mechanism for obtaining information about the fingerprint. Such information may be used to produce images of one or more fingerprints taken from a user.

The invention may include one or more ultrasound imaging systems designed to produce an image of a finger that is similar to images produced by ink-and-paper rolling techniques. Such imaging systems are herein referred to as "curved-surface imaging systems" and the images produced by such systems are referred to as "curved-surface images". One such curved surface imaging system is described in U.S. patent application Ser. No. 10/982,614 and its accompanying U.S. patent application 60/517,808. The description of Ser. No. 10/982,614 and 60/517,808 are hereby incorporated by reference as a means to reduce the size of this application. Such curved-surface imaging systems may be used to produce an image of a finger that is placed on a curved-surface imaging platen, and such images may include details of the fingerprint found on side regions of the finger without requiring the user to roll his finger. By not requiring the user to roll his finger, distortions from stretching and bunching of the skin and fat of finger, which are normally encountered in traditional ink-and-paper rolling techniques, may be avoided.

The invention may also include a planar imaging system. One such planar imaging system is described in U.S. patent application 60/536,816. The description of 60/536,816 is hereby incorporated by reference. Such planar imaging systems may be used to produce an image of one or more fingers that are placed on a substantially planar imaging platen.

The invention described in this application may be embodied as a device having (1) a planar imaging system to enable collection of information from multiple fingers at one time (2) a set of curved-surface imaging systems, and (3) a housing that protects the imaging systems and presents the imaging systems to a user in a manner that is ergonomically convenient to the user. Each curved-surface imaging system may have a curved platen of a size different from others of the curved-surface imaging systems so as to accommodate varying sizes of fingers. For example, there may be four curved-surface imaging systems, and one of those systems may have a platen sized for a pointer finger, one sized for a middle finger, one sized for a ring finger and one sized for a little finger. In this fashion, a user may sequentially insert each of his fingers in the corresponding curved-surface imaging system to enable collection of information that may be used to generate an image of each of the four fingers that is similar to images produced by ink-and-paper rolling techniques.

An image obtained from the planar imaging system is sometimes referred to herein as a "slap image". Such slap images may include features of a hand, for example four fingers held together and scanned as a single image. A slap image may be used to map relational geometries of the various fingers to each other, and the image may be separated and compared with the individual curved-surface images so that the images may be verified as to their correct relational positions, i.e., the right index is indeed the right index, etc. In this manner, the invention described herein may enhance enrollment of fingerprint images into a biometric fingerprint database and may enable the information collection process to proceed with built-in checks to maintain a high degree of accuracy and decrease the time needed to obtain a set of fingerprints from a user.

BRIEF DESCRIPTION OF THE DRAWINGS

For a fuller understanding of the nature and objects of the invention, reference should be made to the accompanying drawings and the subsequent description. Briefly, the drawings are:

FIG. 3, which depicts an embodiment of the device depicted in FIG. 1 in which the imaging system are selectively removable;

FIGS. 4A, 4B and 4C, which are front, side and top views respectively of a curved-surface imaging system module according to the invention;

FIG. 6, which is a perspective view of a thumb guide according to the invention.

FURTHER DESCRIPTION OF THE INVENTION

Figure 1:
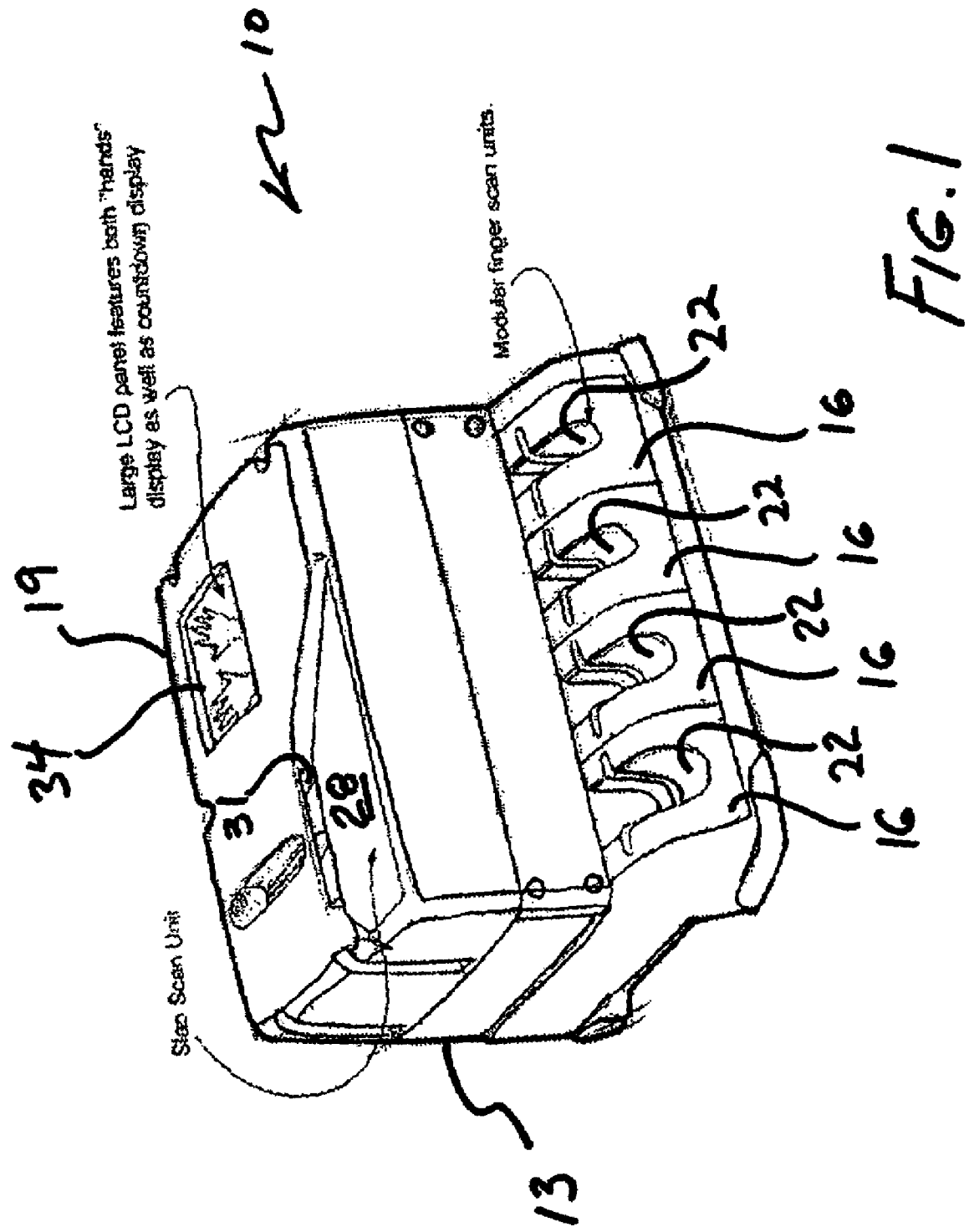
FIG. 1, which is a perspective view of a device according to the invention.
Figure 2A:
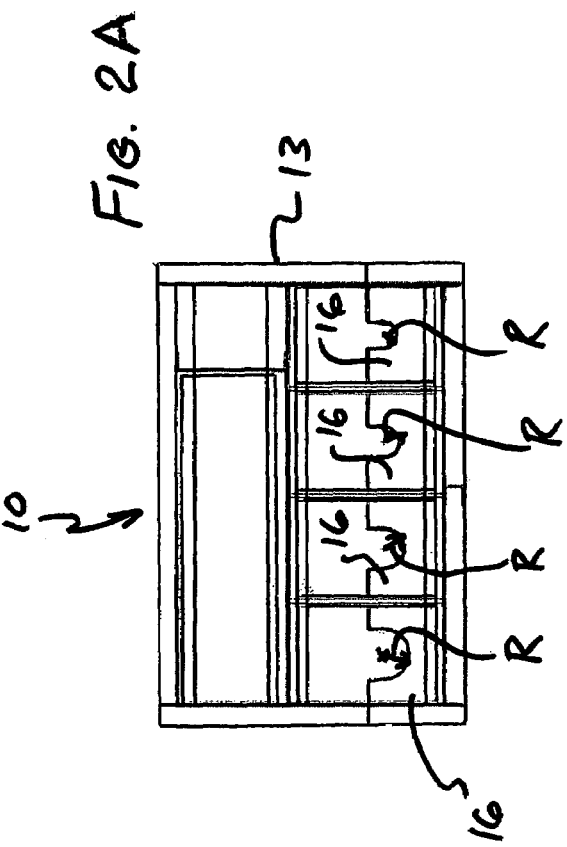
FIGS. 2A, 2B and 2C, which are front, side and top views respectively of the device depicted in FIG. 1.
Figure 2C:
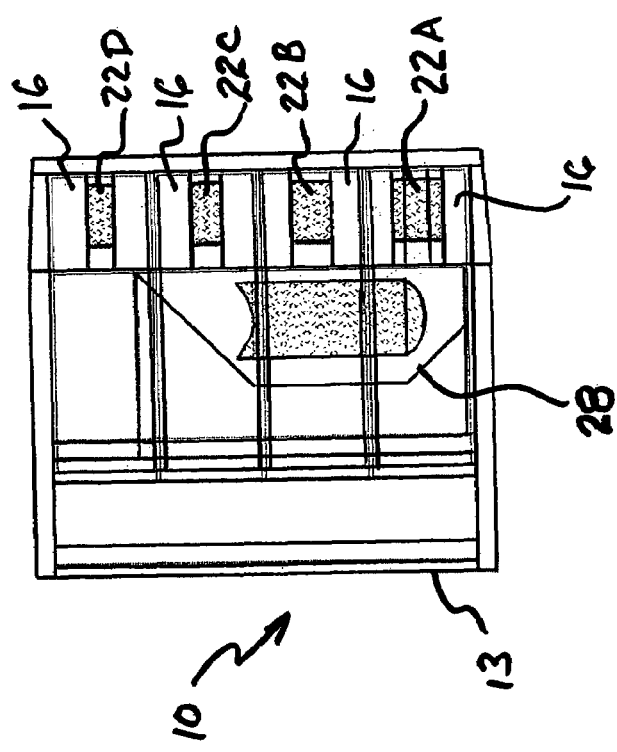
Figure 2B:
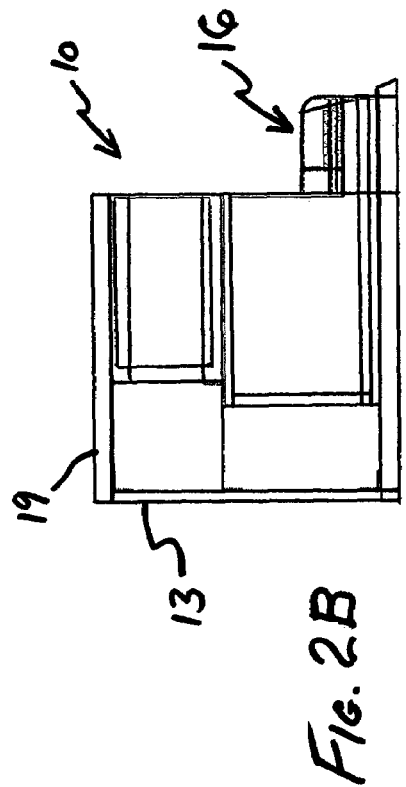

FIG. 1 and FIGS. 2A, 2B and 2C depict a device 10 that includes features of the invention. The device 10 shown in FIG. 1 and FIGS. 2A, 2B and 2C has a housing 13, four curved-surface imaging systems 16 and a planar imaging system 19. Each of the curved-surface imaging systems 16 may be capable of collecting information that may be used to produce a curved-surface image of a finger. The planar imaging system 19 may be capable of collecting information that may be used to produce a planar image of one or more fingers at a time. The curved-surface imaging systems may each include a curved platen 22, and the planar imaging system 19 may include a substantially planar imaging platen 28.

The curved-surface imaging systems 16 may each include a platen 22 having a curved surface. The embodiment shown in FIG. 1 and FIGS. 2A, 2B and 2C has four curved-surface imaging systems 16, each with a different sized platen 22. The platen 22A on the far left side of FIG. 1 has a radius of curvature R that is larger than the radius of curvature R of the platen 22D on the far right side of the device 10 depicted in FIG. 1. The two platens 22B, 22C between the far left platen 22A and the far right platen 22D may have radii of curvature R that are different from the other platens 22A, 22D, and the radii of curvature R of these platens 22B, 22C may be similar or different from each other. In this manner, the radius of curvature R of a particular curved-surface imaging system 16 may be sized to accommodate a finger of an anticipated size. By anticipating the size of the finger, it is believed that a clearer and more accurate image of the finger may be obtained.

Figure 5B:
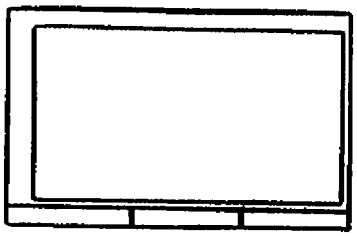
FIGS. 5A, 5B and 5C, which are front, side and top views respectively of a planar imaging system module according to the invention.
Figure 5C:
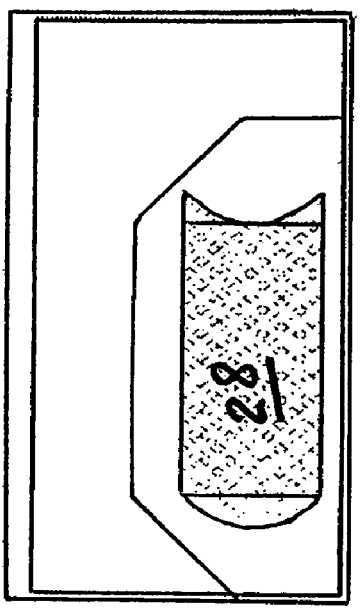
Figure 5A:
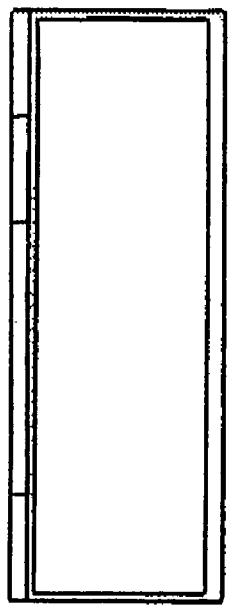

FIG. 3 is an exploded view of the device depicted in FIG. 1. FIG. 3 illustrates an embodiment of the invention in which the curved-surface imaging systems 16 are selectively removable from the housing 10. FIGS. 4A, 4B and 4C depict one such curved-surface imaging system 16. Further, the planar imaging system 19 may also be selectively removable from the housing 10. FIGS. 5A, 5B and 5C depict one such planar imaging system 19. Such an arrangement may be thought of as being modular in nature, with each of the imaging systems 16, 19 being a module that is selectively removable from the housing 10. By providing imaging systems 16, 19 that are selectively removable, the device 10 may be configured for different users. For example the device 10 may be configured for use by adults and then reconfigured for use by children by providing imaging systems 16, 19 having differently sized platens 22, 28 for each type of user. Further, by providing imaging systems 16, 19 that are selectively removable, the device 10 may be more easily serviced when one or more of the imaging systems 16, 19 requires repair or replacement. The imaging systems 16, 19 may be made selectively removable by means of screws 25 that engage the housing 13 when it is desired to attach an imaging system 16, 19 to the housing 13, and which may be removed when it is desired to remove an imaging system 16, 19 from the housing 13.

In an embodiment of the invention, the platens 22, 28 of the imaging systems 16, 19 may be selectively removable. By allowing for removal of one or more of the platens 22, 28, the size of the platens 22, 28 may be changed to accommodate use by different users without changing the remainder of the imaging system 16, 19. Further, damaged platens 22, 28 may be more easily replaced in such a device 10. In one embodiment, a platen 22, 28 may be attached to its imaging system 16, 19 by means of screws, and the screws may be removed when it is desired to change a platen 22, 28.

An embodiment of the invention may include a thumb guide 31. FIG. 6 depicts a thumb guide 31 that is in keeping with the invention. The thumb guide 31 may be selectively extendable from the housing 13, and positionable relative to the planar imaging system 19 so as to position a thumb on a substantially planar imaging platen 28 of the planar imaging system 19. In this manner, the thumb guide 31 may be used to properly position a user's thumb on the planar imaging platen 28 in order to facilitate obtaining image information about the thumb. Such a selectively extendable thumb guide 31 may enable use of the thumb guide 31 when desired, and concealment of the thumb guide 31 when not desired.

An embodiment of the invention may include a display 34 that is capable of providing information to a user of the device 10. The display 34 may provide written instructions that guide the user in the proper use of the device 10. The display 34 may provide an image generated from information obtained by the planar imaging system 19 or the curved-surface imaging system 16, or both. The display 34 may use an LCD (liquid crystal display) as the mechanism for providing viewable information to the user.

U.S. patent application 60/632,152 includes descriptions of embodiments of the invention, and provides further information of the embodiments described herein. For brevity, the disclosure of U.S. patent application 60/632,152 has not been repeated here, but the disclosure found in U.S. patent application 60/632,152 is hereby incorporated by reference.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A fingerprint scanner, comprising:
    a housing;
    a curved-surface imaging system within the housing, the curved-surface imaging system having an arcuately movable ultrasound transducer capable of collecting ultrasound information that may be used to produce a curved-surface image of a finger;
    a planar imaging system within the housing, the planar imaging system being capable of collecting ultrasound information that may be used to produce a planar image of one or more fingers at a time.

2. The scanner of claim 1, wherein the curved-surface imaging system includes a platen having a curved surface.

3. The scanner of claim 2, wherein the platen is selectively removable from the housing.

4. The scanner of claim 2, wherein the curved surface has a radius of curvature suitable for imaging a finger of an anticipated size.

5. The scanner of claim 1, further comprising a thumb guide that is selectively positionable relative to the planar imaging system so as to position a thumb on a substantially planar imaging platen of the planar imaging system in order to facilitate obtaining image information about the thumb.

6. The scanner of claim 5, wherein the thumb guide is selectively extendable from the housing to enable use of the thumb guide when desired, and concealment of the thumb guide when not desired.

7. The scanner of claim 1, further comprising a display capable of providing information to a user.

8. The scanner of claim 1, wherein the curved surface imaging system and the planar imaging system are removable from the housing.

* * * * *